(12) United States Patent
Khedekar

(10) Patent No.: US 11,360,236 B1
(45) Date of Patent: Jun. 14, 2022

(54) SYSTEM FOR MAPPING AND MONITORING EMISSIONS AND AIR POLLUTANT LEVELS WITHIN A GEOGRAPHICAL AREA

(71) Applicant: Prathamesh Khedekar, Downers Grove, IL (US)

(72) Inventor: Prathamesh Khedekar, Downers Grove, IL (US)

(73) Assignee: Prathamesh Khedekar, Downers Grove, IL (US)

( * ) Notice: Subject to any disclaimer, the term of this patent is extended or adjusted under 35 U.S.C. 154(b) by 0 days.

(21) Appl. No.: 17/577,061

(22) Filed: Jan. 17, 2022

(51) Int. Cl.
| | | |
|---|---|---|
| *G01W 1/08* | (2006.01) | |
| *B64C 39/02* | (2006.01) | |
| *G06V 20/17* | (2022.01) | |
| *G16Y 20/10* | (2020.01) | |
| *G16Y 40/10* | (2020.01) | |

(52) U.S. Cl.
CPC ............ *G01W 1/08* (2013.01); *B64C 39/024* (2013.01); *G06V 20/17* (2022.01); *G16Y 20/10* (2020.01); *G16Y 40/10* (2020.01); *B64C 2201/042* (2013.01); *B64C 2201/125* (2013.01); *B64C 2201/127* (2013.01); *B64C 2201/141* (2013.01)

(58) Field of Classification Search
CPC ......... G01W 1/08; G16Y 20/10; G16Y 40/10; G06V 20/17; B64C 2201/042; B64C 2201/125; B64C 2201/127; B64C 2201/141
See application file for complete search history.

(56) References Cited

U.S. PATENT DOCUMENTS

| | | | |
|---|---|---|---|
| 10,866,226 B1* | 12/2020 | Smith | G01N 33/0036 |
| 11,175,202 B2* | 11/2021 | Mohr, Jr. | G05D 1/0094 |
| 2006/0011776 A1* | 1/2006 | Maurer | B64C 39/024 244/1 R |
| 2018/0259429 A1* | 9/2018 | Adams | B64C 39/024 |
| 2018/0292374 A1* | 10/2018 | Dittberner | G01N 33/0047 |
| 2020/0135036 A1* | 4/2020 | Campbell | G06T 11/206 |
| 2020/0302243 A1* | 9/2020 | Fryshman | G06V 10/751 |
| 2021/0283439 A1* | 9/2021 | Raucher | G08G 5/0013 |

* cited by examiner

*Primary Examiner* — Benjamin P Lee
(74) *Attorney, Agent, or Firm* — .Tcasce

(57) ABSTRACT

The present disclosure provides a system comprising a plurality of autonomous units within a geographical region, each configured with a sensor array and a cognitive emission and air pollutant mapping module that enables them to map their surrounding environment and sense and overlay pollutant and emissions data onto said map, including cameras and object detection algorithms for tracking and photographing pollutant sources. Each unit securely transmits the fused map and pollutant source data to one or more servers that compile a complete 3D map of the geographical area overlaid with pollution data which is updated in real time, and also notify relevant third parties to action pollutant sources within the area. The system can further comprise a plurality of smart light poles for displaying pollution data and advisory notices to citizens within sub-regions of the area.

17 Claims, 3 Drawing Sheets

SYSTEM FOR MAPPING AND MONITORING EMISSIONS AND AIR POLLUTANT LEVELS WITHIN A GEOGRAPHICAL AREA

FIELD OF INVENTION

The present invention relates generally to systems for monitoring air pollution and emissions. More specifically, the present invention relates to a system for generating a real time 3D map of a geographical region, overlaid and fused with various pollutant and emissions data.

BACKGROUND

As awareness has grown of the importance of environmental conservation and the long-term damage that airborne pollutants can inflict on human health, especially for those living in cities, much focus has been put on building systems for tracking and monitoring emissions and pollutant levels. Indeed, actively tracking the concentration of air pollutants and emissions has been recognized as critical for the safety and wellness of city residents.

There is thus a strong need for municipalities to enable autonomous wireless emission and air pollutant mapping systems that can continuously track the concentration of pollutants and emissions at different altitudes.

Existing systems are heavily reliant on satellite imaging and lack the ability to provide the detailed tracking and monitoring that is required to proactively respond to pollutant sources and mitigate the risks associated therewith. These traditional air toxicity monitoring methods also fail to capture the concentrations of pollutants in different regions and at different altitudes in any great detail.

It is within this context that the present invention is provided.

SUMMARY

The present disclosure provides a system comprising a plurality of autonomous units within a geographical region, each configured with a sensor array and a cognitive emission and air pollutant mapping module that enables them to map their surrounding environment and sense and overlay pollutant and emissions data onto said map, including cameras and object detection algorithms for tracking and photographing pollutant sources. Each unit securely transmits the fused map and pollutant source data to one or more servers that compile a complete 3D map of the geographical area overlaid with pollution data which is updated in real time, and also notify relevant third parties to action pollutant sources within the area. The system can further comprise a plurality of smart light poles for displaying pollution data and advisory notices to citizens within sub-regions of the area.

Thus, according to one aspect of the present disclosure there is provided a system for mapping and monitoring emissions and air pollutant levels within a geographical area, the system comprising a plurality of unmanned aerial vehicles, UAVs, each UAV comprising a wireless communications module, a GPS module, a cognitive emission and air pollutant mapping module, and a sensor array comprising a plurality of air toxicity monitoring sensors, an optical gas imaging camera, an infra-red camera, and 3D camera.

The cognitive emission and air pollutant mapping module of each UAV is configured to process environmental data and emissions and pollutant data from the sensor array in real time to generate a 3D map of its surroundings overlaid with the emissions and pollutant data;

The cognitive emission and air pollutant mapping module of each UAV is further configured to apply a convolutional neural network for object detection to the environmental data from the sensor array to detect and track pollutant and emission sources, and to capture and transmit photographic evidence of the pollutant sources within a geographical area over a secure network alongside the overlaid map data.

The system further comprises one or more servers and databases, the servers being configured to: receive 3D mapping data of a geographical area overlaid with pollution and emissions data and accompanied by photographic evidence of pollutant sources from multiple UAVs; fuse the data from the multiple UAVs to generate a complete overlaid 3D map of the geographical area; encrypt and transmit the fused data over a secure network to a plurality of third parties and a plurality of public displays; and for each evidenced pollutant source, transmit a notification to action the pollutant source to a regulatory third party, accompanied by the photographic evidence of the source captured by the respective UAV.

In some embodiments, the cognitive emission and air pollutant mapping module of each UAV is further configured to encrypt the overlaid 3D mapping data and pollutant source data prior to transmission.

In some embodiments, the one or more servers and databases are housed in one or more centralised geo-redundant data centres.

In some embodiments, the system further comprises a plurality of smart light poles, each comprising a power source, display screen, wireless communications module, and processor configured to receive public safety and advisory notifications from the one or more servers based on real-time air quality, emissions, and pollution data determined by the system for the geographical area in which the light pole is positioned, and to display that information to members of the public.

Furthermore, each smart light pole may be provided with an array of one or more solar panels which are utilised as the main source of power.

In some embodiments, one or more transmissions of the system are made over a public safety grade mission-critical telecommunications network to prevent information tampering.

In some embodiments, one or more of the transmissions sent by the UAVs to the one or more servers are encrypted using an IPSec protocol.

In some embodiments, the emissions and pollutants data captured and overlaid by each UAV sensor array includes a gas concentration map for one or more of the following chemicals: carbon dioxide $CO_2$, oxygen $O_2$, carbon monoxide CO, lead Pb, nitrous oxide $N_2O$, Ozone $O_3$, particulate matter in the air with a diameter of 10 micrometers or less PM10, particulate matter in the air with a diameter of 2.5 micrometers or less PM2.5, sulfur dioxide $SO_2$, methane $CH_4$, hydrofluorocarbons HFCs, benzene, perchloroethylene $C_2Cl_4$, methylene chloride $CH_2Cl_2$.

In some embodiments, the fused overlaid 3D map generated by the one or more servers is continuously updated based on each new transmission received from the plurality of UAVs.

In some embodiments, each UAV is equipped with autonomous navigation software for monitoring pollutants and emissions within a pre-determined designated area within the geographical region monitored by the system.

In some embodiments, the system further comprises one or more drone launch and landing nests for recharging and maintenance, the nests being distributed about the geographical area monitored by the system.

The one or more nests may be positioned on existing public buildings on structures such as libraries.

In some embodiments, the system further comprises one or more autonomous ground units each being equipped with a wireless communications module, a GPS module, a cognitive emission and air pollutant mapping module, and a sensor array comprising a plurality of air toxicity monitoring sensors, an optical gas imaging camera, an infra-red camera, and 3D camera, and being configured in the same manner as the UAVs.

In some embodiments, the convolutional neural network for object detection installed on each cognitive emission and air pollutant mapping module is a YOLOv4 algorithm.

In some embodiments, the geographical region monitored by the system is divided into neighbourhoods by the one or more servers, and an autonomous mapping unit is assigned to map and monitor each neighbourhood.

In some embodiments, the one or more servers are also configured for the secondary use of assisting emergency response services in the event of a natural disaster.

In some embodiments, the one or more servers are also configured for the secondary use of assisting security services in counteracting acts of terrorism and gang violence.

BRIEF DESCRIPTION OF THE DRAWINGS

Various embodiments of the invention are disclosed in the following detailed description and accompanying drawings.

Figure 1:
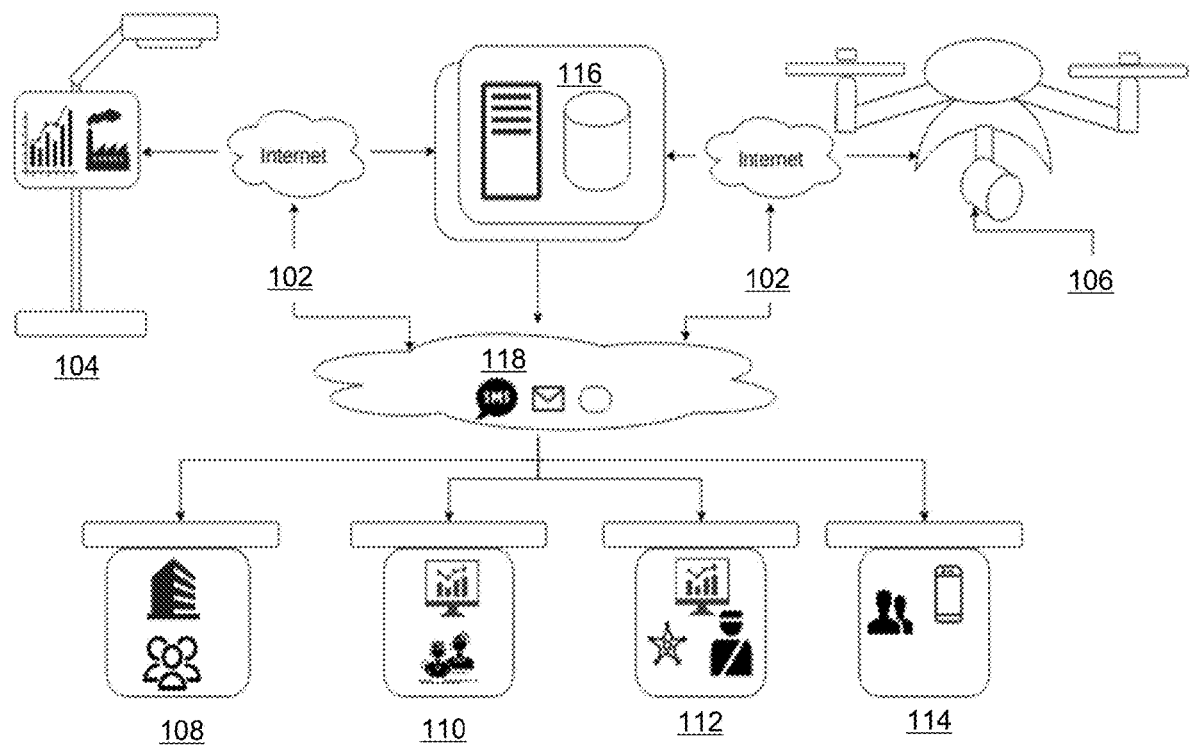
FIG. 1 illustrates an overall view of an example functional system architecture of the present disclosure.

Common reference numerals are used throughout the figures and the detailed description to indicate like elements. One skilled in the art will readily recognize that the above figures are examples and that other architectures, modes of operation, orders of operation, and elements/functions can be provided and implemented without departing from the characteristics and features of the invention, as set forth in the claims.

DETAILED DESCRIPTION AND PREFERRED EMBODIMENT

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

The terminology used herein is for the purpose of describing particular embodiments only and is not intended to be limiting of the invention. As used herein, the term "and/or" includes any combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Referring to FIG. 1, an overall view of an example functional system architecture of the present disclosure is shown, with a swarm of unmanned aerial vehicles 106 collecting pollution and emissions data and transmitting it to one or more geo-redundant data centres 116 comprising a plurality of databases and servers.

Once processed as described below, the emissions and pollution data is transmitted to any number of third parties, and relevant information on air quality/toxicity is displayed to civilians in the geographical area being monitored on a number of smart light poles 104.

The system can operate over any communications network, but preferably operates over a public safety grade LTE telecom network 102. For example, in the United States, the system might operate over Telecom FCC Band 14 in the US. These types of network provide high reliability and security compared to conventional data networks that are used by civilians, and are not impacted by the traffic generated by civilians. The network may also be capable of autonomous healing and self-organization, rendering it highly resistant to network failures.

Each UAV 106 is autonomous and is equipped with a cognitive secure wireless emission and air quality mapping module as described above.

Figure 2:
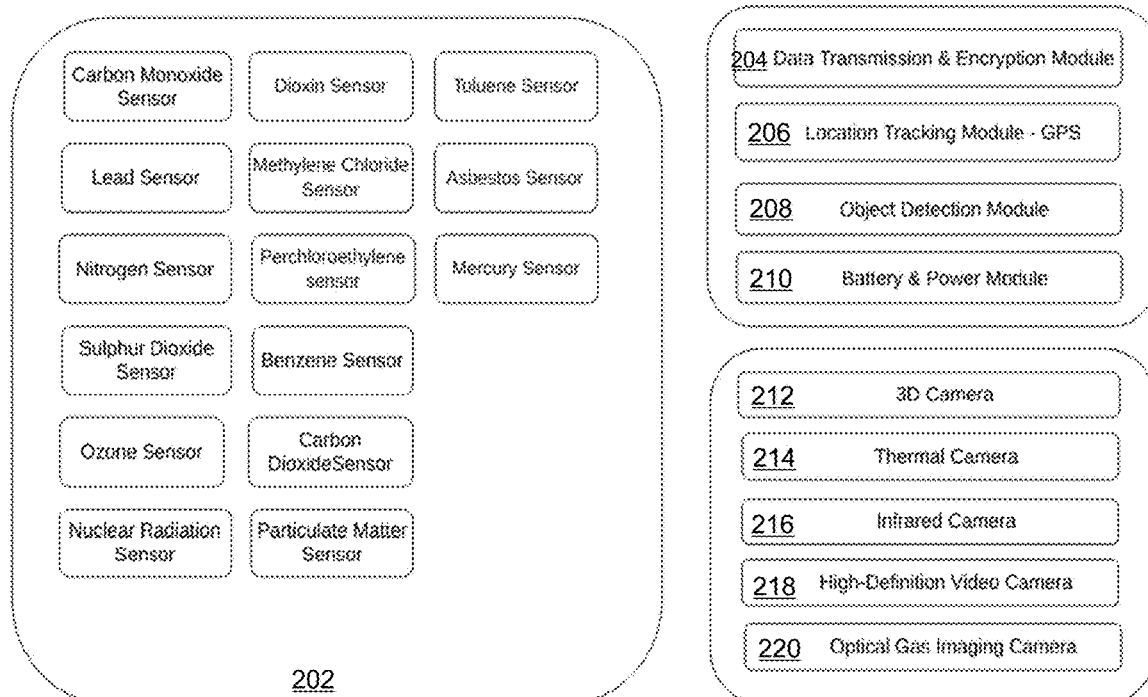
FIG. 2 illustrates a functional block diagram view of the components of an example UAV unit suitable for use in the system of the present disclosure, equipped with a cognitive emission and air pollutant mapping module.

With reference to FIG. 2, a functional block diagram view of the components of an example UAV cognitive secure wireless emission and air quality mapping module suitable for use in the system of the present disclosure is shown.

The module generally comprises a sensor array 202 with a number of specific chemical sensors for detecting air pollutants as listed in the directory of 187 air pollutants US Environmental Protection Agency (US EPA), including but not limited to: Carbon Monoxide (CO), Carbon Dioxide ($CO_2$), Ozone, Lead, Mercury, Cadmium, Methane ($CH_4$), Sulfur Dioxide, Nuclear Radiations, Dioxin, Methylene Chloride, Perchloroethylene, Benzene, Particulate Matter, Toluene, and Asbestos.

The module further comprises a data transmission and encryption module 204 for securely communicating detected pollutant and emissions data to a central server, a location tracking and GPS module 206 for navigation and tracking down pollutant sources, an object detection module 208 for recognising and classifying pollutant sources, a battery and power module 210.

Each UAV will also comprise an array of camera sensors that work in conjunction with the sensor array 202 to capture the concentration of different types of pollutants and gas emissions in a given neighborhood, the array of cameras comprising a 3D camera 212 for mapping the UAVs surroundings, a thermal camera 214 for operating in darkness and to monitor temperature variations in the region and detect smoke, an infrared camera 216, a high definition video camera 218, and an optical gas imaging camera 220 (optical gas imaging is the method of using thermal infrared cameras to visualize gas, including methane and many other organic gases).

The object detection module 208 may employ a convolutional neural network for detecting pollutant sources and cause images of recognised pollutant sources to be taken and transmitted to the central servers through the various cameras. The convolutional neural network may be a YOLOv4 object detection algorithm that is pre-trained to detect different types of objects/anomalies. For example, sources such as fireworks, fire, vehicle emissions, trash, factories, houses emitting smoke, etc might be photographed as evidence of their pollution.

The module also comprises a data and map fusion module in the processor which fuses all the data received through the various sensors and overlays it onto a 3D map of the UAV's surroundings in real time, which may be a particular neighbourhood of a city.

The UAVs themselves may physically take the from of a standard four rotor aerial drone.

Figure 3:
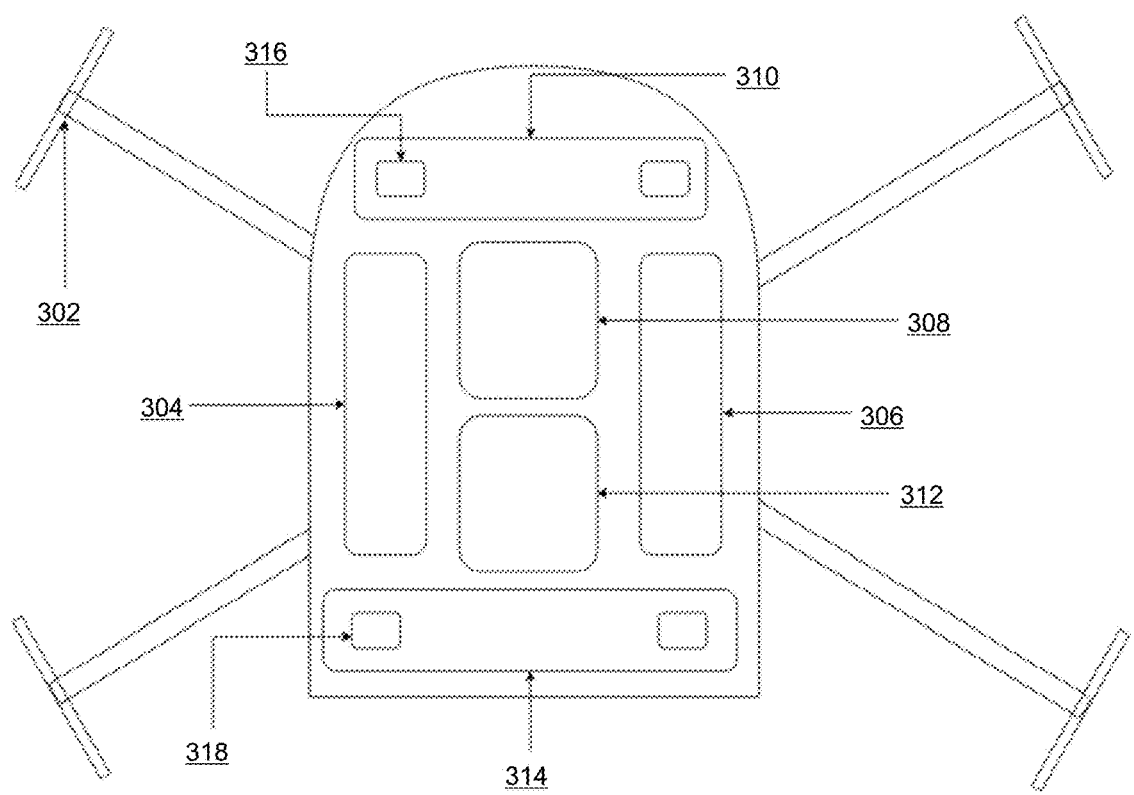
FIG. 3 illustrates a top-down view of an example UAV unit suitable for use in the system of the present disclosure including internal components.
Figure 4:
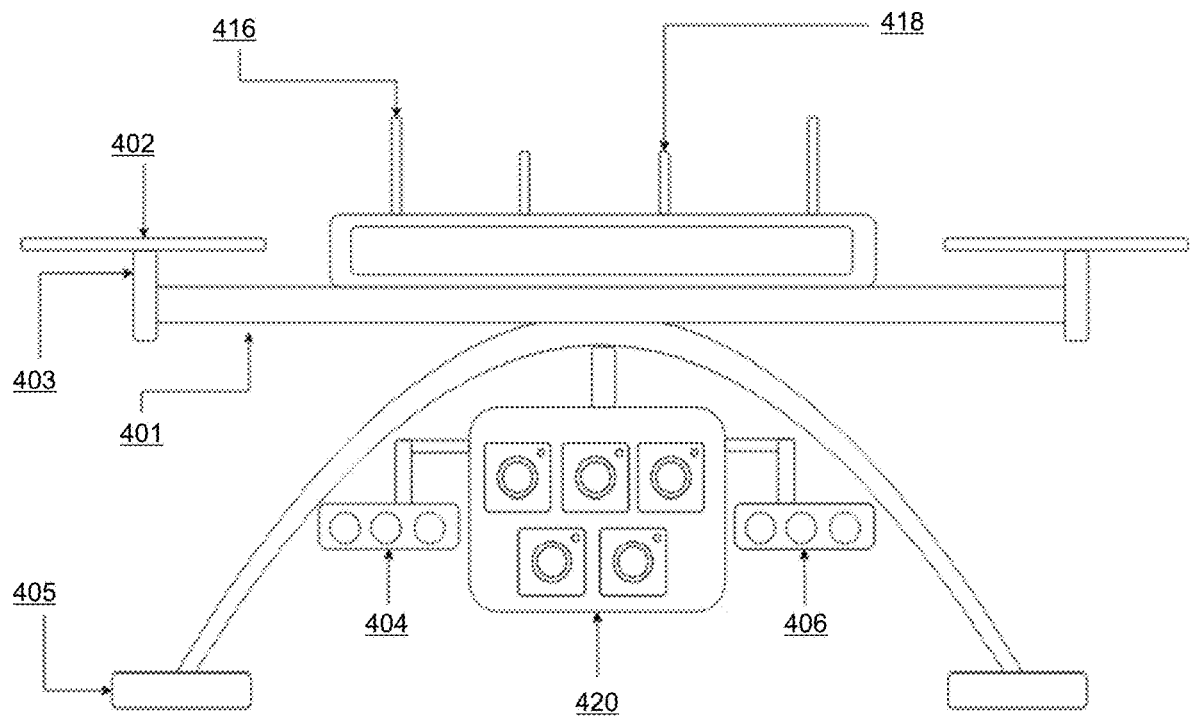
FIG. 4 illustrates a frontal view of the example UAV unit of FIG. 3.

Referring to FIGS. 3 and 4, top-down and frontal views of an example UAV unit suitable for use in the system of the present disclosure are shown, including the internal components of the unit.

As can be seen, the frame 401 of the device is standard, with four propellers 302, 402 each having a corresponding motor 403, at each corner of the unit. The unit also comprises standard landing gear 405, a battery module 308, a telecom data transmission and object detection module 310, trajectory controller module 312, location tracking module 314, telecom antenna 316, 416, GPS antenna 318, 418, as is known to those skilled in the art.

Additionally, the UAV is equipped with a left side air toxicity sensor module 304, 404 and a right side air toxicity sensor module 306, 406, and with a camera array 420 including a 3D camera, optical gas imaging camera, thermal camera, infrared camera, and high definition video camera as described above.

The UAVs (which can also be ground based rover units) may be launched from drone nests as is well known in the art. Such nests may be installed on public buildings such as neighbourhood libraries to avoid the requirement for additional infrastructure.

Returning to FIG. 1, the streams of data captured and processed by the swarm of UAVs in different neighbourhoods will then be transmitted to the centralized servers 116 located in geo-redundant datacenters using public safety grade telecom networks 102.

Each packet of fused 3D map frames transmitted from to the servers will be encrypted to ensure it is not changed by a malicious intermediary device, for example using an IPSec protocol. Images of relevant pollutant source anomalies detected by the object detection neural networks of the UAVs will also be transmitted, such as the source of smoke, gas emissions, fire pits, vehicle emissions, an unattended pile of trash, unattended bodies of dead animals and birds, etc. These two sets of information will be received by the centralized server 116 and will be stored in the database and overlaid on a complete, unified 3D map of a geographical region monitored by the system.

Once processed, the central servers 116 send real-time alert notifications to relevant third parties such as regulatory bodies and authorities, for example in the form of SMS and e-mail notifications, to facilitate quick countermeasures to pollutant sources and levels by local municipality agencies. Such notifications can also be sent to residents in relevant neighbourhoods.

In the present example, the system is configured to notify a drone monitoring team responsible for launching and maintaining the UAV swarm 108, local and national air quality monitoring teams 110, the US environment protection agency 112, and to user devices of local residents 114 via a mobile application.

Exemplary user devices 114 as may be used in combination with the system by having the appropriate software installed thereon include, without limitation, a personal computer (PC), a laptop, a tablet computer, and smartphone. Generally, each user device includes a display and/or one or more processors. Each of the displays offers the user a visual interface for interaction with the system. For example, the system notifications and alerts may be presented as a browser interface that makes use of known techniques for user interaction. In this example, any user device may include conventional software such as productivity tools (e.g., word processing, spreadsheets, etc.) and at least one browser. Tablet computer or smartphone may also include at least one "app" (defined generally as a purpose-oriented application that may include network communications as part of the functionality), as well as a biometric sensor that can be a conventional optical scanner configured with an appropriate app for use as a fingerprint reader. The fingerprint reader may include software for receiving data from the scanner and interpreting the data within the context of a fingerprint. Other user devices may include a biometric sensor and/or other equipment useful for implementing authentication schemes.

Generally, each user device is in communication with the system via network 118 through an internet communications channel. The network 118 is also in communication with server 116 and may further communicate with a database.

In addition to sending alert notifications to third parties, the servers 116 may be configured to communicate with a number of smart light poles 104 equipped with LED dashboard displays and installed in monitored neighbourhoods to cause real-time air toxicity data for said neighbourhoods to be displayed thereon. Corresponding advisory information may also be displayed for residents.

Figure 5:
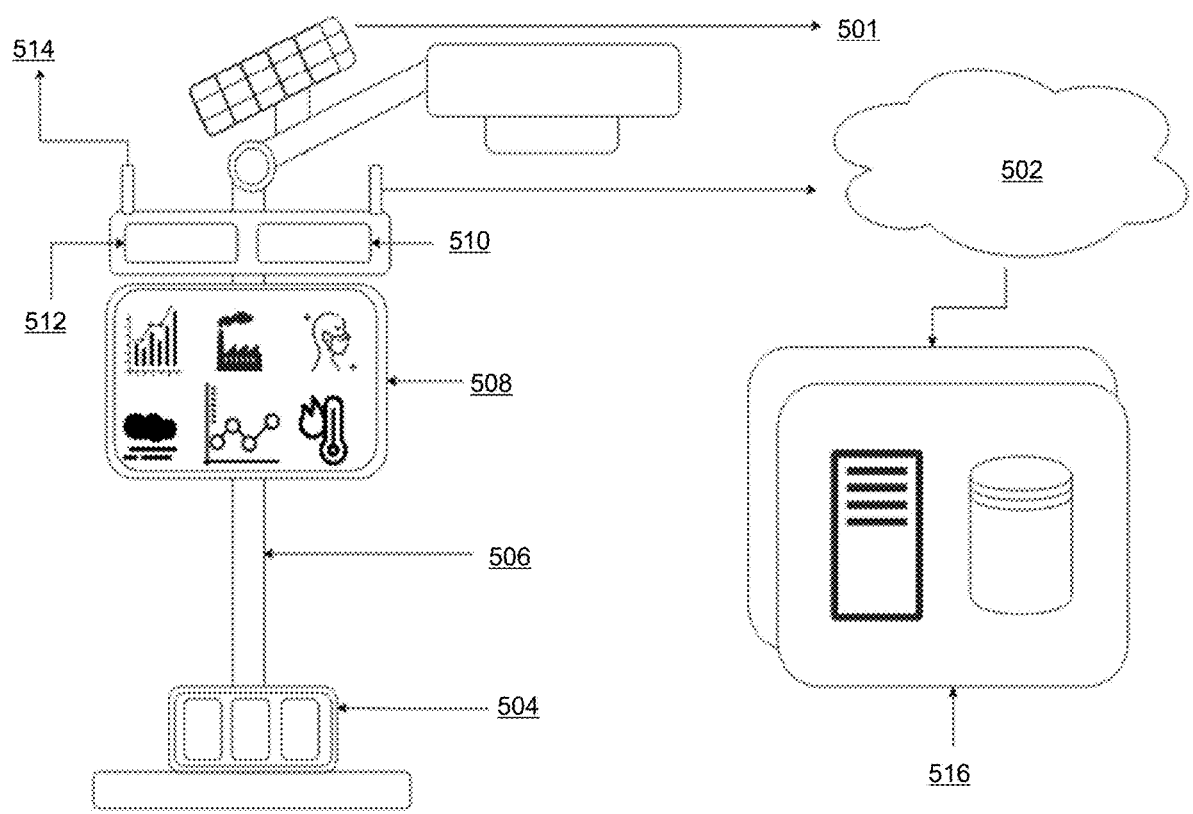
FIG. 5 illustrates a more detailed view of an example smart light pole configuration suitable for use in the system of the present disclosure.

In this manner the system provides a real-time unified view of the concentration of air pollutants and emissions of each neighborhood to residents, local public safety agencies, and to US Environmental Protection Agency (US EPA) and thus plays a key role in maintaining national safety and security Referring to FIG. 5, a more detailed view of an example smart light pole configuration suitable for use in the system of the present disclosure is shown.

The light pole comprises a solar panel 501 which can be used as a main power source when there is sufficient solar light available, a back-up battery power source 504, the light pole structure itself 506, an air toxicity advisory LED display 508, a data transmission telecom module 510 for communicating with the system, a single board computer 512 for processing transmissions received from the servers 516 over LTE telecom network 502, and a data transmission antenna 514.

The smart light poles will not only display the air toxicity statistics but can be used by the national air quality monitoring team (US EPA) to convey advisory notices such as recommending the use of masks to residents in case the emission levels in certain neighbourhoods are higher than regulatory safety limits.

In addition to the purposes described above, the system can have the secondary function of responding to natural disasters, acts of terrorism, and gang violence.

For example, if there are events such as forest fires, earthquakes, storms, tornado, flash floods, major riots, etc the public safety agencies can use this system to monitor those events using these drones and relaying information and advisory to people using the LED dashboards mounted on each pole and using mobile software and SMS alerts.

In a similar manner, the system also can be used as an added layer for national emergency response by public safety agencies (Firefighter, Police Officers, Paramedics).

Since the drones are equipped with sensors and cameras and are pre-deployed in various regions the public safety agencies can use this system for situational awareness in the event of terrorism and gang-related activities within the country.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit)

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Unless otherwise defined, all terms (including technical terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

The disclosed embodiments are illustrative, not restrictive. While specific configurations of the pollution and emissions mapping and monitoring system have been described in a specific manner referring to the illustrated embodiments, it is understood that the present invention can be applied to a wide variety of solutions which fit within the scope and spirit of the claims. There are many alternative ways of implementing the invention.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A system for mapping and monitoring emissions and air pollutant levels within a geographical area, the system comprising:
    a plurality of unmanned aerial vehicles, UAVs, each UAV comprising a wireless communications module, a GPS module, a cognitive emission and air pollutant mapping module, and a sensor array comprising a plurality of air toxicity monitoring sensors, an optical gas imaging camera, an infra-red camera, and 3D camera;
    wherein the cognitive emission and air pollutant mapping module of each UAV is configured to process environmental data and emissions and pollutant data from the sensor array in real time to generate a 3D map of its surroundings overlaid with the emissions and pollutant data;
    wherein the cognitive emission and air pollutant mapping module of each UAV is further configured to apply a convolutional neural network for object detection to the environmental data from the sensor array to detect and track pollutant and emission sources, and to capture and transmit photographic evidence of the pollutant sources within a geographical area over a secure network alongside the overlaid map data;
    one or more servers and databases, the servers being configured to:
        receive 3D mapping data of a geographical area overlaid with pollution and emissions data and accompanied by photographic evidence of pollutant sources from multiple UAVs;
        fuse the data from the multiple UAVs to generate a complete overlaid 3D map of the geographical area;
        encrypt and transmit the fused data over a secure network to a plurality of third parties and a plurality of public displays; and
        for each evidenced pollutant source, transmit a notification to action the pollutant source to a regulatory third party, accompanied by the photographic evidence of the source captured by the respective UAV.

2. A system according to claim 1, wherein the cognitive emission and air pollutant mapping module of each UAV is further configured to encrypt the overlaid 3D mapping data and pollutant source data prior to transmission.

3. A system according to claim 1, wherein the one or more servers and databases are housed in one or more centralised geo-redundant data centres.

4. A system according to claim 1, wherein the system further comprises a plurality of smart light poles, each comprising a power source, display screen, wireless communications module, and processor configured to receive public safety and advisory notifications from the one or more servers based on real-time air quality, emissions, and pollution data determined by the system for the geographical area in which the light pole is positioned, and to display that information to members of the public.

5. A system according to claim 4, wherein each smart light pole is further provided with an array of one or more solar panels which are utilised as the main source of power.

6. A system according to claim 1, wherein one or more transmissions of the system are made over a public safety grade mission-critical telecommunications network to prevent information tampering.

7. A system according to claim 1, wherein one or more of the transmissions sent by the UAVs to the one or more servers are encrypted using an IPSec protocol.

8. A system according to claim 1, wherein the emissions and pollutants data captured and overlaid by each UAV sensor array includes a gas concentration map for one or more of the following chemicals: carbon dioxide $CO_2$, oxygen $O_2$, carbon monoxide CO, lead Pb, nitrous oxide $N_2O$, Ozone $O_3$, particulate matter in the air with a diameter of 10 micrometers or less PM10, particulate matter in the air with a diameter of 2.5 micrometers or less PM2.5, sulfur dioxide $SO_2$, methane $CH_4$, hydrofluorocarbons HFCs, benzene, perchloroethylene $C_2Cl_4$, methylene chloride $CH_2Cl_2$.

9. A system according to claim 1, wherein the fused overlaid 3D map generated by the one or more servers is continuously updated based on each new transmission received from the plurality of UAVs.

10. A system according to claim 1, wherein each UAV is equipped with autonomous navigation software for monitoring pollutants and emissions within a pre-determined designated area within the geographical region monitored by the system.

11. A system according to claim 1, wherein the system further comprises one or more drone launch and landing nests for recharging and maintenance, the nests being distributed about the geographical area monitored by the system.

12. A system according to claim 11, wherein the one or more nests are positioned on existing public buildings on structures such as libraries.

13. A system according to claim 1, wherein the system further comprises one or more autonomous ground units each being equipped with a wireless communications module, a GPS module, a cognitive emission and air pollutant mapping module, and a sensor array comprising a plurality of air toxicity monitoring sensors, an optical gas imaging camera, an infra-red camera, and 3D camera, and being configured in the same manner as the UAVs.

14. A system according to claim 1, wherein the convolutional neural network for object detection installed on each cognitive emission and air pollutant mapping module is a YOLOv4 algorithm.

15. A system according to claim 1, wherein the geographical region monitored by the system is divided into neighbourhoods by the one or more servers, and an autonomous mapping unit is assigned to map and monitor each neighbourhood.

16. A system according to claim 1, wherein the one or more servers are also configured for the secondary use of assisting emergency response services in the event of a natural disaster.

17. A system according to claim 1, wherein the one or more servers are also configured for the secondary use of assisting security services in counteracting acts of terrorism and gang violence.

* * * * *